United States Patent
Diffendal

[19]

[11] Patent Number: 5,906,213
[45] Date of Patent: May 25, 1999

[54] FLOSSING DEVICE AND METHOD OF USE

[76] Inventor: Steven Gloyd Diffendal, 10835 Green Castle St., Santee, Calif. 92071

[21] Appl. No.: 09/083,558

[22] Filed: May 22, 1998

[51] Int. Cl.⁶ ..................................................... A61C 15/00
[52] U.S. Cl. ........................................... 132/309; 132/322
[58] Field of Search ................................... 132/309, 322, 132/323, 324; 433/82, 88; 601/162, 163, 165

[56] References Cited

U.S. PATENT DOCUMENTS

| | | |
|---|---|---|
| 213,997 | 4/1879 | Merrill . |
| 1,417,848 | 5/1922 | Mac Donald ........................... 132/324 |
| 1,464,013 | 8/1923 | Roberts . |
| 1,700,690 | 1/1929 | Stafford . |
| 3,368,553 | 2/1968 | Kirby ........................................ 128/62 |
| 3,472,247 | 10/1969 | Borsum . |
| 3,830,247 | 8/1974 | Kaphalakos . |
| 3,902,510 | 9/1975 | Roth . |
| 4,031,908 | 6/1977 | Ting . |
| 4,319,595 | 3/1982 | Ulrich ..................................... 132/322 |
| 4,883,080 | 11/1989 | Lang ....................................... 132/322 |
| 5,094,256 | 3/1992 | Barth ...................................... 132/322 |
| 5,365,956 | 11/1994 | Guadiana ................................ 132/309 |
| 5,570,709 | 11/1996 | Haddad et al. ......................... 132/322 |
| 5,582,195 | 12/1996 | Nagel ..................................... 132/321 |

FOREIGN PATENT DOCUMENTS

| | | | |
|---|---|---|---|
| 91/07143 | 5/1991 | WIPO | .................................... 132/324 |

*Primary Examiner*—Todd E. Manahan
*Attorney, Agent, or Firm*—Eric Karich, Esq.

[57] ABSTRACT

A dental cleaning tool has a handle, a base, a floss stem, and a supply of dental floss. The dental floss is contained within the base and a supply of fluid is contained within the handle. The base and the handle removably engage each other, frictionally clamping one end of the dental floss therebetween. Both the fluid and the other end of the dental floss exit through a fluid ejection conduit of the base. The floss is removably engaged to a floss locking tip near the terminal end of the floss stem, allowing the user to utilize the dental floss to clean his teeth. While flossing his teeth, the user can squeeze the handle and spray fluid, such as mouth wash, down the length of the dental floss and into his mouth.

19 Claims, 3 Drawing Sheets

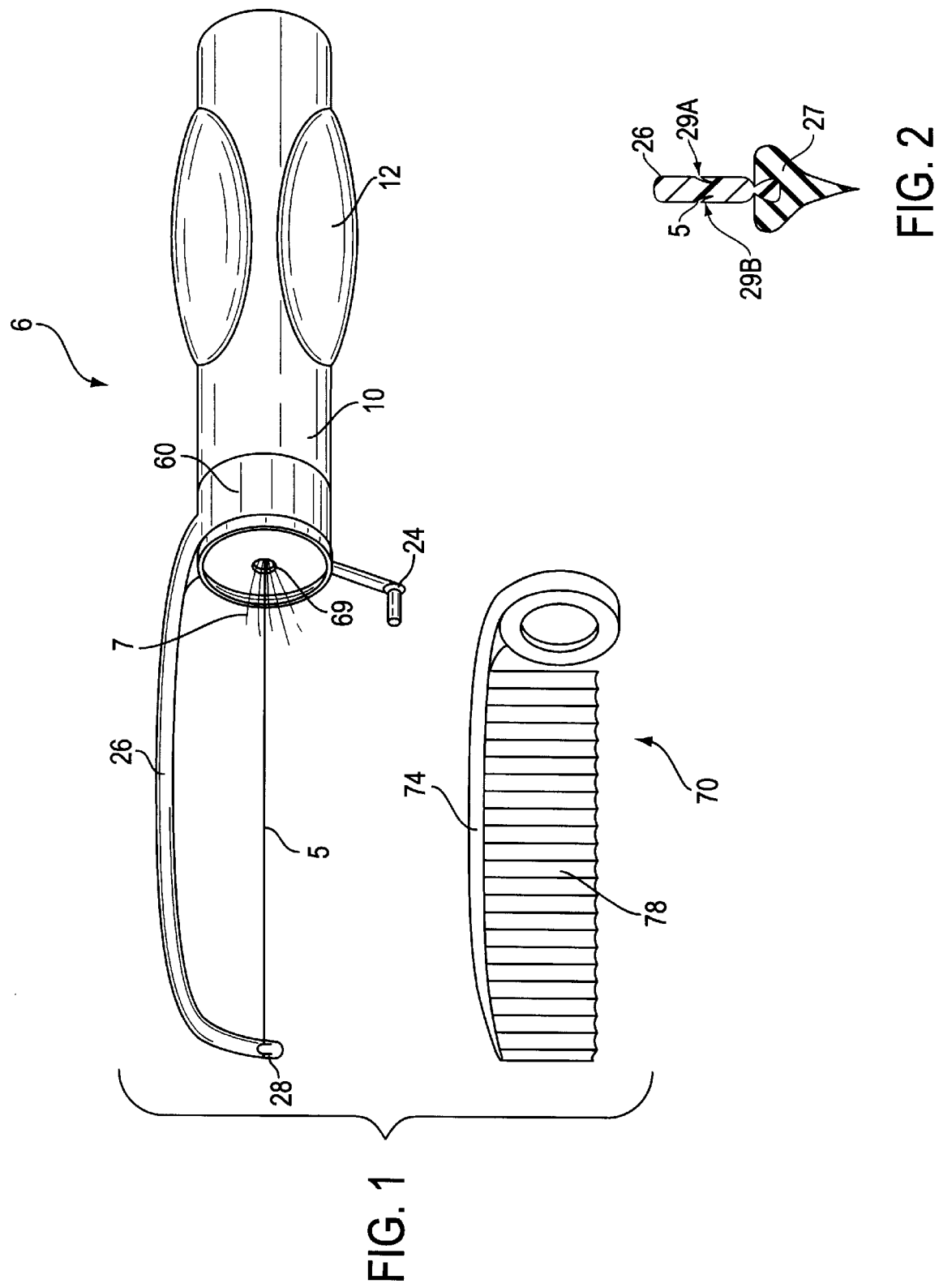

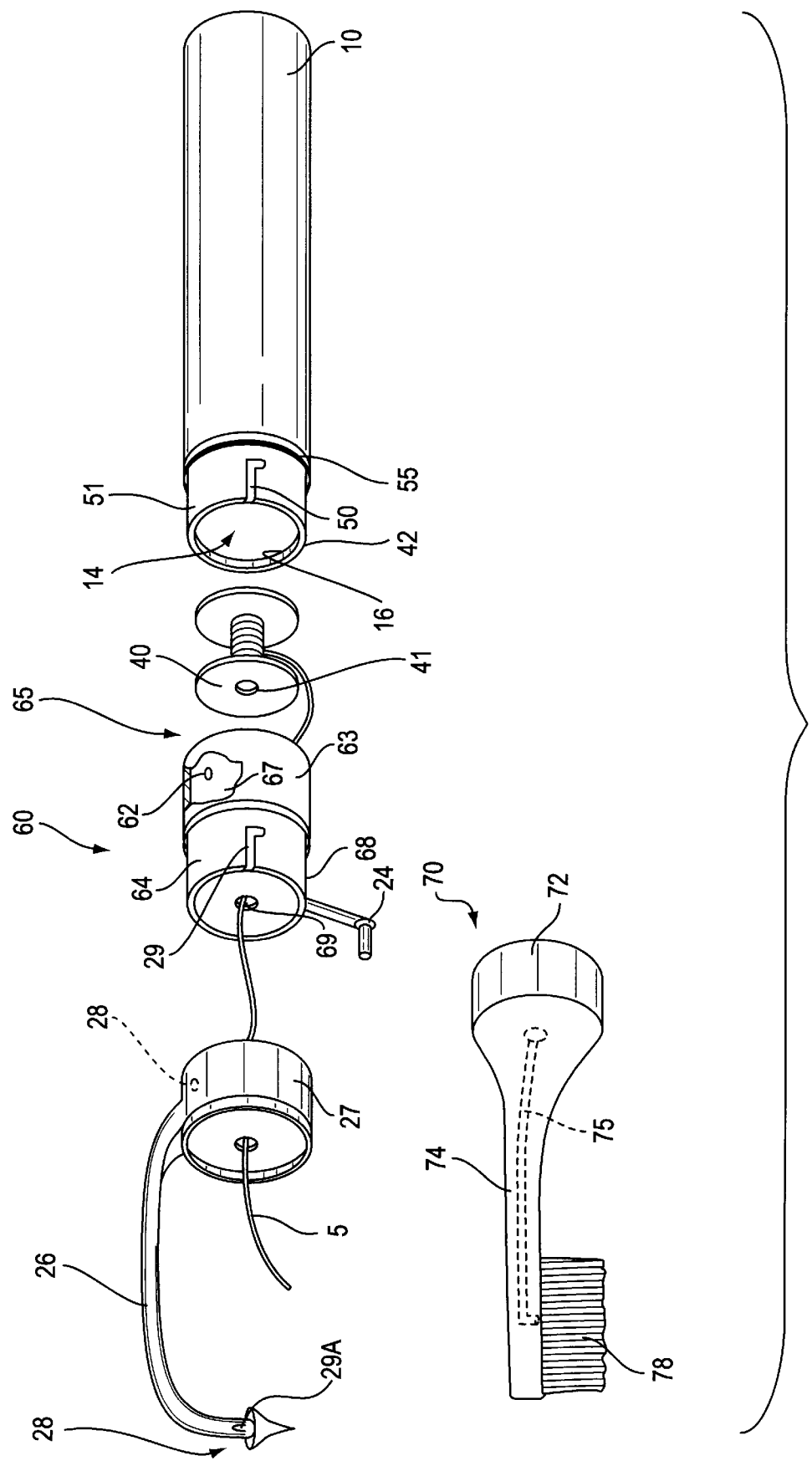

FLOSSING DEVICE AND METHOD OF USE

BACKGROUND OF THE INVENTION

1. Field of the Invention

This invention relates generally to flossing devices and their methods of use, and more particularly to a flossing device that contains both floss and mouthwash, clamps the floss for use, and sprays the mouthwash down the length of clamped floss and between the user's teeth when desired.

2. Description of Related Art

The prior art teaches various flossing devices that combine a supply of floss with various locking arms to hold the floss for use. These include Guadiana, U.S. Pat. No. 5,365,956, Barth, U.S. Pat. No. 5,094,256, and Lang, U.S. Pat. No. 4,883,080. Similar devices were developed as early as 1879. Some of the earliest patents of this nature include Stafford, U.S. Pat. No. 1,700,690, Roberts, U.S. Pat. No. 1,464,013, and Merrill, U.S. Pat. No. 213,997. The advantage of these devices is that the dispenser serves the second purpose of holding the floss for easy use, without requiring the user to use his fingers to hold the floss.

The prior art also teaches various devices that contain both dental floss and mouthwash or other antiseptic fluids. Roth, U.S. Pat. No. 3,902,510, teaches a jar of mouthwash having a separate container of dental floss, the dental floss being pulled across an applicator that is soaking in the mouthwash. Nagel, U.S. Pat. No. 5,582,195, teaches a jar of mouthwash that contains a supply of dental floss, the dental floss being actually soaking within the mouthwash. None of these devices, however, teach a structure that can actually be used to facilitate flossing.

Finally, the prior art also teaches various devices that combine flossing devices with mouthwash dispensing devices. Kirby, U.S. Pat. No. 3,368,553, teaches a tooth cleaning and massage device that can be adapted, in two different embodiments, to either clamp a length of dental floss for use in flossing, or dispense a supply of mouthwash. Borsum, U.S. Pat. No. 3,472,247, teaches a hydraulic-filament dental device that both clamps a length of dental floss and shoots a stream of fluid in the vicinity of the floss, the stream of fluid thereby cleaning the user's teeth while he flosses. Ting, U.S. Pat. No. 4,031,908, teaches a dental appliance having means for flossing and a means for discharging a jet of water closely adjacent to the floss to rinse the teeth being flossed. These devices are designed to be hooked up to an external source of water such as a pump or a water faucet. Furthermore, the dental floss is maintained separately from the water. Finally, the water is dispensed from a conduit separate from the floss.

The prior art teaches flossing devices that include both a supply of dental floss and a supply of fluid. However, the prior art does not teach that a device that stores the dental floss and mouthwash in the same container as well as dispense the two products from the same conduit. The present invention achieves this structure in a very simple, easy to manufacture device that fulfills the needs of the user, and provides further related advantages as described in the following summary.

SUMMARY OF THE INVENTION

The present invention teaches certain benefits in construction and use which give rise to the objectives described below.

The present invention provides a dental cleaning tool and method of use. The dental cleaning tool has a handle, a base, a floss stem, and a supply of dental floss. The dental floss is contained within the base and a supply of fluid is contained within the handle. The base and the handle removably engage each other, frictionally clamping one end of the dental floss therebetween. Both the fluid and the other end of the dental floss exit through a fluid ejection conduit of the base. The floss is removably engaged to a floss locking tip near the terminal end of the floss stem, allowing the user to utilize the dental floss to clean his teeth. While flossing his teeth, the user can squeeze the handle and spray fluid, such as mouth wash, down the length of the dental floss and into his mouth.

A primary objective of the present invention is to provide a dental cleaning tool and method of use having advantages not taught by the prior art.

Another objective is to provide a dental cleaning tool that clamps the dental floss for easy use and also sprays mouthwash down the length of the dental floss and into the user's mouth, cleaning and moistening the both the dental floss and the user's mouth.

Another objective is to provide a dental cleaning tool having a floss stem that pulls back the user's lips to further facilitate flossing.

Another objective is to provide a supply of dental floss that is stored in mouthwash so that it is maintained in a moist and disinfected state.

Another objective is to provide a dental cleaning tool that can easily convert to a toothbrush, the toothbrush being positioned to be sprayed with mouthwash and thus receiving the same benefits as the flossing attachment.

Another objective is to provide a dental cleaning tool that is small and easy to carry for travel, while still providing the above described benefits.

A further objective is to provide a dental cleaning tool having few parts, making the tool cheap and easy to manufacture.

Other features and advantages of the present invention will become apparent from the following more detailed description, taken in conjunction with the accompanying drawings, which illustrate, by way of example, the principles of the invention.

BRIEF DESCRIPTION OF THE DRAWING

The accompanying drawings illustrate the present invention. In such drawings:

FIG. 1 is a perspective view of a first embodiment of the present invention;

FIG. 2 is a partial sectional view of a floss locking tip, showing an embodiment that includes a pick on the terminal end of floss locking tip;

FIG. 4 is an exploded partial cut away perspective view of a second embodiment of the invention.

DETAILED DESCRIPTION OF THE INVENTION

Figure 3:
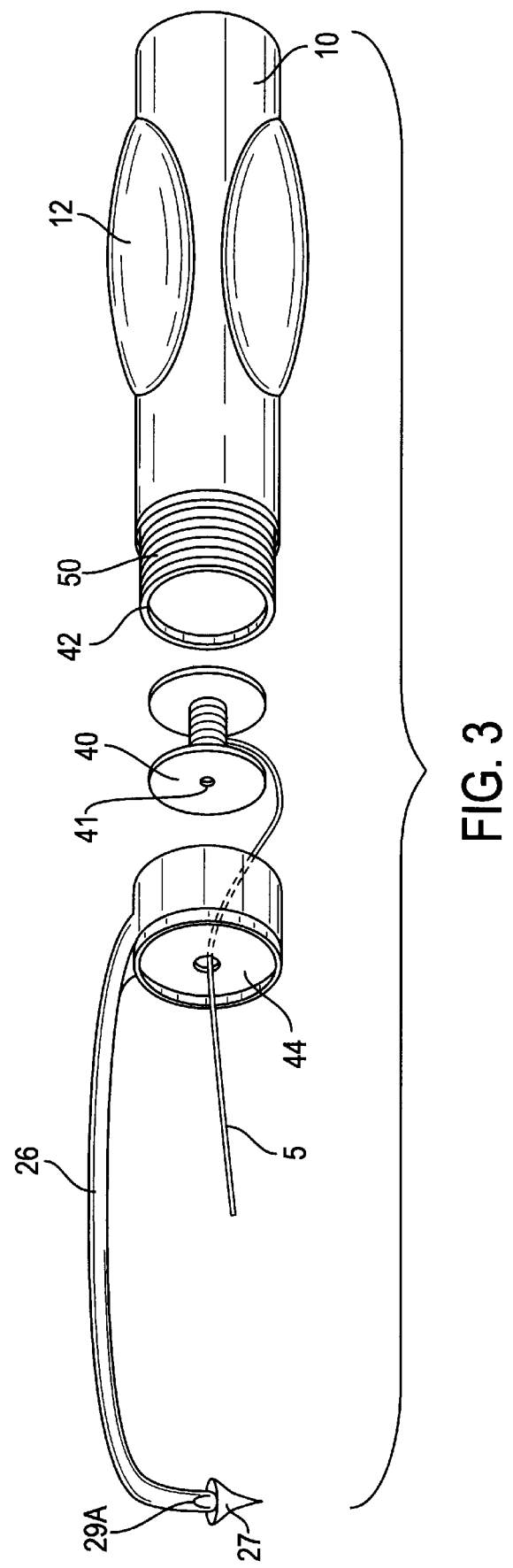
FIG. 3 is an exploded perspective view of FIG. 1.

The above described drawing figures illustrate the invention, a dental cleaning tool 6 having a handle 10, a base 60, a floss stem 26, and a supply of dental floss 5. The dental floss 5 is contained within the base 60 and a supply of fluid 7 is contained within the handle 10. The base 60 and the handle 10 removably engage each other, frictionally clamping one end of the dental floss 5 therebetween. Both the fluid 7 and the other end of the dental floss 5 exit through a fluid ejection conduit 69 of the base 60. The floss is removably engaged to a floss 5 locking tip 28 near the terminal end of the floss stem 26, allowing the user to utilize the dental floss 5 to clean his teeth. While cleaning his teeth, the user can squeeze the handle 10 and spray the fluid 7, such as mouth wash, down the length of the dental floss 5 and into his mouth.

The floss stem 26 is attached to the base 60, preferably extending outward in a roughly C-shape. The floss stem 26 is preferably made of fairly rigid molded plastic and should be approximately 1.5 inches long. While a longer floss stem 26 may be necessary, as in FIGS. 1 and 3, to accommodate the toothbrush 70 attachment, a shorter floss stem 26 is preferred. The shorter floss stem 26 not only fits more easily into the user's mouth, it also provides a greater tension in the dental floss 5. The floss stem 26 has a floss locking tip 28 at its terminal end opposite the base 60. The floss locking tip 28 is preferably a first and second locking slots 29A and 29B located on either side of the floss stem 26. The first and second slots 29A and 29B are preferably positioned parallel to the floss stem 26, and the second locking slot 29B further including a floss cutting element (not shown).

In one embodiment, as shown in FIGS. 1 and 3, the floss stem 26 is integrally attached to the base 60. This embodiment is cheaper to manufacture, but it is limited in its ability to allow further attachments, such as the toothbrush 70 described below. In the preferred embodiment, the floss stem 26 removably engages the base 60. In this embodiment, the floss stem 26 further includes a base receiving means 27 that removably engages a stem attachment means of the base 60, the base receiving means 27 providing a fluid opening coaxial to and in fluid transmission with the fluid ejection conduit 69. There are many removable connections known in the art that serve this purpose. In the preferred embodiment, the stem attachment means is a cylindrical element that slides into the base receiving means 27. The base receiving means 27 preferably includes a first locking pin 28 that removably engages a base locking slot 29 in the stem attachment means 64 of the base 60. In an alternative embodiment, the first locking pin 28 and the base locking slot 29 are not used, and the connection relies on a tight frictional fit. In another alternative embodiment, as shown in FIG. 3, the base receiving means 27 threadedly engages the stem attachment means 64.

The primary benefit of the removable floss stem 26 is that it can be replaced with a variety of alternative attachments. A toothbrush 70 having a elongate body 74 and a plurality of bristles 78 can be attached to the stem receiving means as long as it includes a toothbrush base receiving means 72 similar to the floss stem 26. Such a toothbrush 70 preferably further includes a toothbrush conduit 75 which communicates from the fluid ejection conduit 69 to the bristles 78. If the floss stem 26 is integrally attached to the base 60, as shown in FIG. 1, the elongate body 74 of the toothbrush 70 is removably engagable to the floss stem 26 with a frictional fit between the floss stem 26 and the base 60. As long as the elongate body 74 does not cover the fluid ejection conduit 69, the user can spray the fluid 7 onto the bristles 78 directly in this configuration.

The handle 10 has an internal chamber 14 and a fluid escape aperture 16. The internal chamber 14 is capable of containing the fluid. The fluid escape aperture 16 communicates with the internal chamber 14. The fluid 7 escape aperture 16 has an aperture rim 42. The handle 10 includes a means for forcing the fluid out of the fluid escape aperture 16, thereby squirting the fluid through the fluid ejection conduit 69 and down the dental floss 5. The means for forcing the fluid out is preferably achieved by making at least part of the handle 10 flexible. When the user squeezes the handle 10, the fluid 7 is forced out the fluid escape aperture 16. The handle 10 is preferably a cylindrical device about 3–4 inches long and 0.5–1 inches in diameter. In its preferred embodiment, as shown in FIG. 4, the handle 10 is made of a flexible plastic. In an alternative embodiment, as shown in FIGS. 1 and 3, the handle 10 is made of a rigid plastic frame containing a flexible rubber bladder 12. The rigid plastic frame 10 is shaped to allow the user access to the rubber bladder 12. By squeezing the rubber bladder 12, the user forces the fluid 7 out the fluid escape aperture 16.

The base 60 has a fluid transmission conduit 65 communicating between the fluid escape aperture 16 of the handle 10 and a fluid ejection conduit 69 of the base 60. The fluid transmission conduit 65 of the base 60 further includes a floss storage chamber 67 for containing the spool 40 containing the dental floss 5. The fluid ejection conduit 69 has a diameter only slightly larger than the dental floss 5, so when the user sprays the fluid 7 through the fluid ejection conduit 69, it comes out with some force, rather than simply dribbling out of a larger hole. This spray of fluid is useful for further cleaning and freshening the user's mouth. The base 60 is preferably cylindrical in shape and made of fairly rigid molded plastic. The base 60 is preferably as small as possible, being just large enough to contain the spool 40 of dental floss 5 and attach to the handle 10 and the floss stem 26. The base 60 removably engages the handle 10 to cover the fluid escape aperture 16. In its preferred mode, the base 60 removably engages the handle 10 through the cooperation of a handle receiving means 63 of the base 60 and a base attachment means 51 of the handle 10. It is preferred that the base 60 be removable from the handle 10 so that the user can add more fluid to the handle 10 and more dental floss 5 to the base 60. This configuration also provides a simple mechanism to anchor the dental floss 5 for use. A disposable version could be designed with an integral connection, however, without changing the novelty of this invention. As described above, the two elements could be removably attached with threaded or frictional connections. In the preferred embodiment, the handle receiving means 63 of the base 60 is a second locking pin 62 and the base attachment means 51 of the handle 10 is a handle locking slot 50. A rubber sealing ring 55 is preferably added to prevent leakage.

The supply of dental floss 5, preferably stored on a spool 40, is positioned within the fluid transmission conduit 65 of the base 60, preferably in a floss storage chamber 67 that is shaped to snugly contain the spool 40. The spool 40 preferably includes a spool conduit 41 that allows passage of the fluid through the spool 40. When the handle 10 is attached to the base 60, an inner portion of the dental floss 5, the portion on the spool 40, is frictionally clamped between the handle 10 and the base 60. An outer end of the dental floss 5 which has been unwound from the spool 40, is threaded through the fluid ejection conduit 69 of the base 60 and clamped in the floss locking tip 28 of the floss stem 26.

In its preferred embodiment, the invention further includes a flexible pick 27 attached to the terminal end of the floss stem 26 opposite the base 60. This pick 27 allows the user to clean and massage his gums after flossing. The invention preferably further includes a flexible plug 24. The plug 24 is preferably attached in proximity to the fluid ejection conduit 69, most preferably to the base 60. The flexible plug 24 is shaped to fit within and seal the fluid ejection conduit 69, to prevent leakage of fluid from the handle 10.

This invention further includes a method of cleaning teeth with the above described device. The method includes the steps of first providing a handle 10 having an internal chamber 14 and a fluid escape aperture 16, the fluid escape aperture 16 communicating with the internal chamber 14, the internal chamber 14 being capable of containing the fluid 7. Next, the user provides a base 60 having an fluid transmission conduit 65, the fluid transmission conduit 65 having a floss storage chamber 67. The user then provides a floss stem 26 attached to the base 60, the floss stem 26 having a floss locking tip 28 at a terminal end. Finally, the user provides a supply of dental floss 5, preferably on a spool 40, and fills the internal chamber 14 of the handle 10 with the fluid 7, preferably mouthwash. The dental floss 5 is positioned within the floss storage compartment of the fluid transmission conduit 65 of the base 60. The dental floss 5 is then threaded through the fluid ejection conduit 69 of the base 60. The base 60 is then removably engaged to the handle 10 to cover the fluid escape aperture 16, frictionally clamping the dental floss 5 between the handle 10 and the base 60. Once the device is assembled, the dental floss 5 that is protruding from the fluid ejection conduit 69 is pulled tight and clamping the dental floss 5 in the floss locking tip 28 of the floss stem 26, positioning the dental floss 5 for use. If not enough of the dental floss 5 is available, the handle 10 can be partially removed from the base 60, releasing the spool 40 of floss, allowing the user to pull a greater amount of the floss out for use. The user can then floss with the dental floss 5. Furthermore, by squeezing the handle 10, the user can spray the fluid 7 through the fluid ejection conduit 69, down the length of the dental floss 5 and into the user's mouth.

While the invention has been described with reference to at least one preferred embodiment, it is to be clearly understood by those skilled in the art that the invention is not limited thereto. Rather, the scope of the invention is to be interpreted only in conjunction with the appended claims.

What is claimed is:

1. A dental cleaning tool comprising:
   a handle having an internal chamber and a fluid escape aperture, the fluid escape aperture communicating with the internal chamber, the internal chamber containing a fluid;
   a base that removably engages the handle to cover the fluid escape aperture, the base having a fluid transmission conduit communicating between the fluid escape aperture of the handle and a fluid ejection conduit of the base;
   a floss stem attached to the base, the floss stem having a floss locking tip at a terminal end;
   a supply of dental floss positioned within the fluid transmission conduit of the base, the dental floss having an inner portion that is frictionally clamped between the handle and the base when they are engaged, and an outer end that is threaded through the fluid ejection conduit of the base and clamped in the floss locking tip of the floss stem; and
   a means for forcing the fluid out of the fluid escape aperture, thereby squirting the fluid through the fluid ejection conduit and down the dental floss.

2. The dental cleaning tool of claim 1 wherein the floss stem is integrally attached to the base.

3. The dental cleaning tool of claim 2 further comprising a toothbrush having a elongate body and a plurality of bristles, the elongate body removably engaging the floss stem.

4. The dental cleaning tool of claim 3 wherein the elongate body is removably engagable to the floss stem with a frictional fit between the floss stem and the base.

5. The dental cleaning tool of claim 1 wherein the floss stem removably engages the base.

6. The dental cleaning tool of claim 5 wherein the floss stem further includes a base receiving means that removably engages a stem attachment means of the base, the base receiving means providing a fluid opening coaxial and in fluid transmission with the fluid ejection conduit.

7. The dental cleaning tool of claim 6 wherein the base receiving means threadedly engages the stem attachment means.

8. The dental cleaning tool of claim 6 wherein the base receiving means includes a first locking pin that removably engages a first locking slot in the stem attachment means.

9. The dental cleaning tool of claim 1 wherein the base removably engages the handle through the cooperation of a handle receiving means of the base and a base attachment means of the handle.

10. The dental cleaning tool of claim 9 wherein the handle receiving means of the base is a second locking pin and the base attachment means of the handle is a second locking slot.

11. The dental cleaning tool of claim 9 wherein the handle receiving means of the base threadedly engages the base attachment means of the handle.

12. The dental cleaning tool of claim 1 further comprising a spool upon which the dental floss is stored, the spool being frictionally clamped between the handle and the base, thereby anchoring the inner portion of the dental floss.

13. The dental cleaning tool of claim 1 further comprising a flexible pick attached to the terminal end of the floss stem.

14. The dental cleaning tool of claim 1 further comprising a flexible plug attached in proximity to the fluid ejection conduit, the flexible plug being shaped to fit within and seal the fluid ejection conduit.

15. A dental cleaning tool comprising:
   a handle having an internal chamber and a fluid escape aperture, the fluid escape aperture communicating with the internal chamber, the internal chamber containing a fluid;
   a base that removably engages the handle to cover the fluid escape aperture, the base having an fluid transmission conduit communicating between the fluid escape aperture of the handle and a fluid ejection conduit of the base;
   a floss stem attached to the base, the floss stem having a floss locking tip at a terminal end;
   a supply of dental floss positioned within the fluid transmission conduit of the base, the dental floss having an inner portion that is frictionally clamped between the handle and the base when they are engaged, and an outer end that is threaded through the fluid ejection conduit of the base and clamped in the floss locking tip of the floss stem; and
   a means for forcing the fluid out of the fluid escape aperture, thereby squirting the fluid through the fluid ejection conduit and down the dental floss.

16. The dental cleaning tool of claim 15 further comprising a spool upon which the dental floss is stored, the spool being frictionally clamped between the handle and the base, thereby anchoring the inner portion of the dental floss.

17. The dental cleaning tool of claim 15 further comprising a flexible pick attached to the terminal end of the floss stem.

18. The dental cleaning tool of claim 15 further comprising a flexible plug attached in proximity to the fluid ejection conduit, the flexible plug being shaped to fit within and seal the fluid ejection conduit.

19. A method of cleaning teeth comprising:

providing a handle having an internal chamber and a fluid escape aperture, the fluid escape aperture communicating with the internal chamber, the internal chamber being capable of containing the fluid;

providing a base having an fluid transmission conduit, the fluid transmission conduit having a floss storage chamber;

providing a floss stem attached to the base, the floss stem having a floss locking tip at a terminal end;

providing a supply of dental floss;

filling the internal chamber of the handle with fluid;

positioning the dental floss within the floss storage compartment of the fluid transmission conduit of the base;

threading the dental floss through the fluid ejection conduit of the base;

removably engaging the base to the handle to cover the fluid escape aperture, frictionally clamping the dental floss between the handle and the base;

pulling the dental floss that is protruding from the fluid ejection conduit tight and clamping the dental floss in the floss locking tip of the floss stem;

flossing with the dental floss; and squeezing the handle to spray the fluid through the fluid ejection conduit, down the length of the dental floss and into the user's mouth.

* * * * *